United States Patent [19]
Sakawa et al.

[11] Patent Number: 5,948,226
[45] Date of Patent: *Sep. 7, 1999

[54] OXYGEN CONCENTRATION DETECTOR

[75] Inventors: Toshihiro Sakawa, Toyohashi; Taiji Yokoyama, Toyoake; Michihiro Yamakawa, Kariya, all of Japan

[73] Assignee: Nippondenso Co., Ltd., Kariya, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/582,476

[22] Filed: Jan. 3, 1996

[30] Foreign Application Priority Data

Jan. 27, 1995 [JP] Japan .................................. 7-031360

[51] Int. Cl.⁶ ................................................. G01N 27/407
[52] U.S. Cl. ......................... 204/424; 204/427; 204/428; 248/314; 248/316.1; 248/316.7; 267/158; 267/159; 267/164; 267/182
[58] Field of Search ..................................... 204/421–429; 248/314, 316.1, 316.7; 267/158, 159, 164, 182

[56] References Cited

U.S. PATENT DOCUMENTS

| | | | |
|---|---|---|---|
| 2,100,042 | 11/1937 | Travis | 248/314 |
| 3,960,692 | 6/1976 | Weyl et al. | 204/428 |
| 4,019,974 | 4/1977 | Weyl et al. | 204/428 |
| 4,121,989 | 10/1978 | Shum et al. | 204/428 |
| 4,184,934 | 1/1980 | Bode et al. | 204/428 |
| 4,540,070 | 9/1985 | Yonovich et al. | 267/141 |
| 4,741,816 | 5/1988 | Nishio et al. | 204/425 |
| 5,098,548 | 3/1992 | Duce | 204/424 |
| 5,435,901 | 7/1995 | Friese et al. | 204/424 |

FOREIGN PATENT DOCUMENTS 3-61566   6/1991   Japan .

*Primary Examiner*—T. Tung
*Attorney, Agent, or Firm*—Pillsbury Madison & Sutro LLP

[57] ABSTRACT

An oxygen concentration detector easily assembled without producing conducting malfunctions at an external electrode includes a cylindrical housing and a detecting element being inserted into and disposed inside the housing. Powdery seal materials made of ceramic power are filled under pressure between a top portion of the detecting element and the housing. The detecting element has the external electrode at an external surface thereof and a lead portion extending upwardly from the external electrode. A ring-shaped conducting member is installed between the lead portion of the detecting element and the housing as a ground to conduct electricity therebetween and has a resilient contacting piece in contact with the lead portion at an inner peripheral portion of the ring-shaped conducting member.

27 Claims, 8 Drawing Sheets

OXYGEN CONCENTRATION DETECTOR

CROSS REFERENCE TO RELATED APPLICATION

This application is based on and claims priority of Japanese Patent Application No. Hei 7-31360 filed Jan. 30, 1995, the content of which is incorporated herein by reference.

BACKGROUND OF THE INVENTION

1. Field of the Invention

The present invention relates to an oxygen concentration detector used for air fuel ratio control or the like in an automotive engine.

2. Description of Related Art

As shown in FIG. 14, conventionally, an oxygen concentration detector 9 has a cylindrical housing 10 and a detecting element 12 inserted into and disposed in the cylindrical housing 10. Powdery seal materials 13 made of ceramic powder are filled under pressure between a top portion of the detecting element 12 and the housing 10. The detecting element 12 has an external electrode 121 at an external surface thereof.

The detecting element 12 includes a generally test-tube-shaped solid electrolyte, the external electrode 121 installed at the external surface of the solid electrolyte, an air chamber made inside the solid electrolyte and an internal electrode provided at an interior surface of the solid electrolyte. The external electrode 121 is connected to a lead wire from a connecting piece 181 through a terminal 18 to be conducted to ground. The connecting piece 181 is installed at a lead portion 122 extending toward an upper portion of the detecting element 12 from the external electrode 121.

The internal electrode is connected to the lead wire from a connecting piece 191 through a terminal 19 in such a manner that the internal electrode is connected to an external circuit. The connecting piece 191 is installed at a lead portion 124 extending toward an upper portion of the detecting element 12 from the internal electrode.

Since the oxygen concentration detector 9 has a small size of a few centimeters, a lead wire having a small diameter is used. This kind of lead wire is easily broken, and therefore, an operational malfunction of the oxygen concentration detector 9 occurs. Also, since both the connecting pieces 181 and 191 are disposed close to each other, shorting may occur between the connecting pieces 181 and 191.

In order to prevent the pieces from shorting, a head portion of the detecting element 12 has a stepped structure. However, processing the detecting element 12 takes time.

Conventionally, an oxygen concentration detector in which the detecting element 12 is assembled in the housing 10 in such a manner that the external electrode 121 is in contact with the housing 10 and the oxygen concentration detector 9 is grounded at the housing 10 is disclosed. By providing metallic packing or the like between the external electrode 121 and the housing 10 and using elasticity of the packing or a similar property, electric conduction between the housing 10, the external electrode 121 and the metallic packing can be more reliably ensured.

However, problems in the above-described oxygen concentration detector are found. That is, in the oxygen concentration detector, a front surface of the metallic packing is oxidized because components in the measured gas have high temperatures, and therefore, a conducting malfunction may occur between the external electrode 121 and the housing 10.

Further, when the oxygen concentration detector is installed at a position where oxygen is to be detected, although the oxygen concentration detector is fixed by a screw portion 104 provided at the housing 10, the housing 10 is deformed and a contacting malfunction may occur.

In order to protect the external electrode 121 from corrosive material contained in the measured gas, a protecting layer is usually provided at the external surface of the external electrode 121. Since the protecting layer is a porous film made of ceramic particles or the like, when the protecting layer is extended to a contacting portion with the metallic packing even though the detecting element 12 makes contact with the housing 10 through the metallic packing, electric conduction is not obtained between the detecting element 12 and the housing 10. Without providing the protecting layer, the external electrode 121 may be damaged by the corrosive material.

SUMMARY OF THE INVENTION

In view of the foregoing problems, it is a primary object of the invention to provide an oxygen concentration detector capable of being assembled easily without having a conducting malfunction at an external electrode.

In the present invention, an oxygen concentration detector has a cylindrical housing and a detecting element inserted into and disposed inside the housing. Powdery seal materials made of ceramic powder are filled under pressure between a top portion of the detecting element and the housing. The detecting element has an internal electrode at an interior surface thereof and an external electrode at an external surface thereof and a lead portion extending upwardly from the external electrode. In the oxygen concentration detector, a ring-shaped conducting member is installed between the lead portion of the external electrode at the detecting element and the housing to conduct electricity therebetween. The ring-shaped conducting member has a resilient contacting piece in contact with the lead portion of an inner periphery portion of the ring-shaped conducting member.

A remarkable feature of the present invention is that the ring-shaped conducting member is installed between the lead portion of the detecting element and the housing to conduct electricity therebetween. The ring-shaped conducting member includes a ring-shaped body and an inserting portion for inserting the detecting element installed at an inner periphery portion of the body. The ring-shaped conducting member is in contact with the housing or with a metallic part in contact with the housing at an outer periphery portion of the body to conduct electricity.

The external surface of the detecting element is covered with, for example, a platinum film or the like. In the platinum film, a portion for carrying out oxygen concentration detection by making contact with measured gas is the external electrode and a portion without being in contact with the measured gas is the lead portion. The ring-shaped conducting member is installed between the lead portion and the housing. The housing is a ground.

The lead portion is mainly an upward portion from a portion in which the powdery seal materials are filled. The detecting element is of a glass and laminated layer type and the detecting element can have a heater individually or integrally inside it. In this case, a heating portion at the heater is positioned at a tip end portion of the detecting element.

Next, a plurality of resilient contacting pieces are preferably provided at the inner periphery portion of the ring-shaped conducting member. A resilient piece in contact with the housing is preferably provided at the outer periphery portion of the ring-shaped conducting member. Further, the resilient piece at the outer periphery portion has a plurality of resilient contacting pieces.

By having the above-described structure, the ring-shaped conducting member, the detecting element, the housing and the like can be in contact with one another more securely. The contacting malfunction when the detecting element and the housing are deformed due to assembly of the conventional detecting element and change in temperature of the oxygen concentration detector can be prevented.

In the oxygen concentration detector according to the present invention, the ring-shaped conducting member is installed between the lead portion of the detecting element and the housing to conduct electricity therebetween. Therefore, electric conduction between the external electrode and the housing which is a ground can be obtained without using a thin lead wire which is easily broken. As a result, an oxygen concentration detector having high reliability at the conducting portion at the external electrode can be obtained.

The conducting portion disposing the ring-shaped conducting member and positioning between the lead portion and the housing is a upper portion of the detecting element, which has a low temperature. That is, even though a heater for maintaining the external electrode with an element activating temperature at the detecting element is installed inside the detecting element, the upper portion of the detecting element is away from the heater and the measured gas with high temperature, and therefore, the upper portion has a low temperature. Therefore, heating oxidization at the conducting portion can be prevented and conducting malfunctions due to the oxidization can be prevented.

In an assembling process of the oxygen concentration detector, an assembling operation of a terminal and the lead wire to the external electrode can be eliminated. Thus, performance of the assembling operation is increased.

The lead portion for conducting electricity to the internal electrode is installed at a head portion of the detecting element. The ring-shaped conducting member is disposed to surround an outer periphery of the detecting element below the head portion. Thus, shorting between the external electrode and the internal electrode does not occur.

A resilient contacting piece is installed at the inner periphery portion of the ring-shaped conducting member and the ring-shaped conducting member and the detecting element are in contact with each other by the resilient contacting piece. Therefore, regardless of deformation of the detecting element and the housing, the ring-shaped conducting member and the detecting element are always in contact with each other.

According to the present invention, an oxygen concentration detector which can be easily assembled without producing conducting malfunctions at the external electrode can be obtained.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PRESENTLY PREFERRED EMBODIMENTS

The preferred embodiments of the present invention are hereinafter described with reference to the accompanying drawings.

(First Embodiment)

An oxygen concentration detector according to a first embodiment of the present invention is explained with reference to the accompanying drawings.

An oxygen concentration detector 1 of the first embodiment is used as an air-fuel ratio sensor of an automotive engine, and by its housing 10, the oxygen concentration detector 1 is fixed to a metallic part of the engine such as an outside exhaust manifold or the like.

Figure 1:
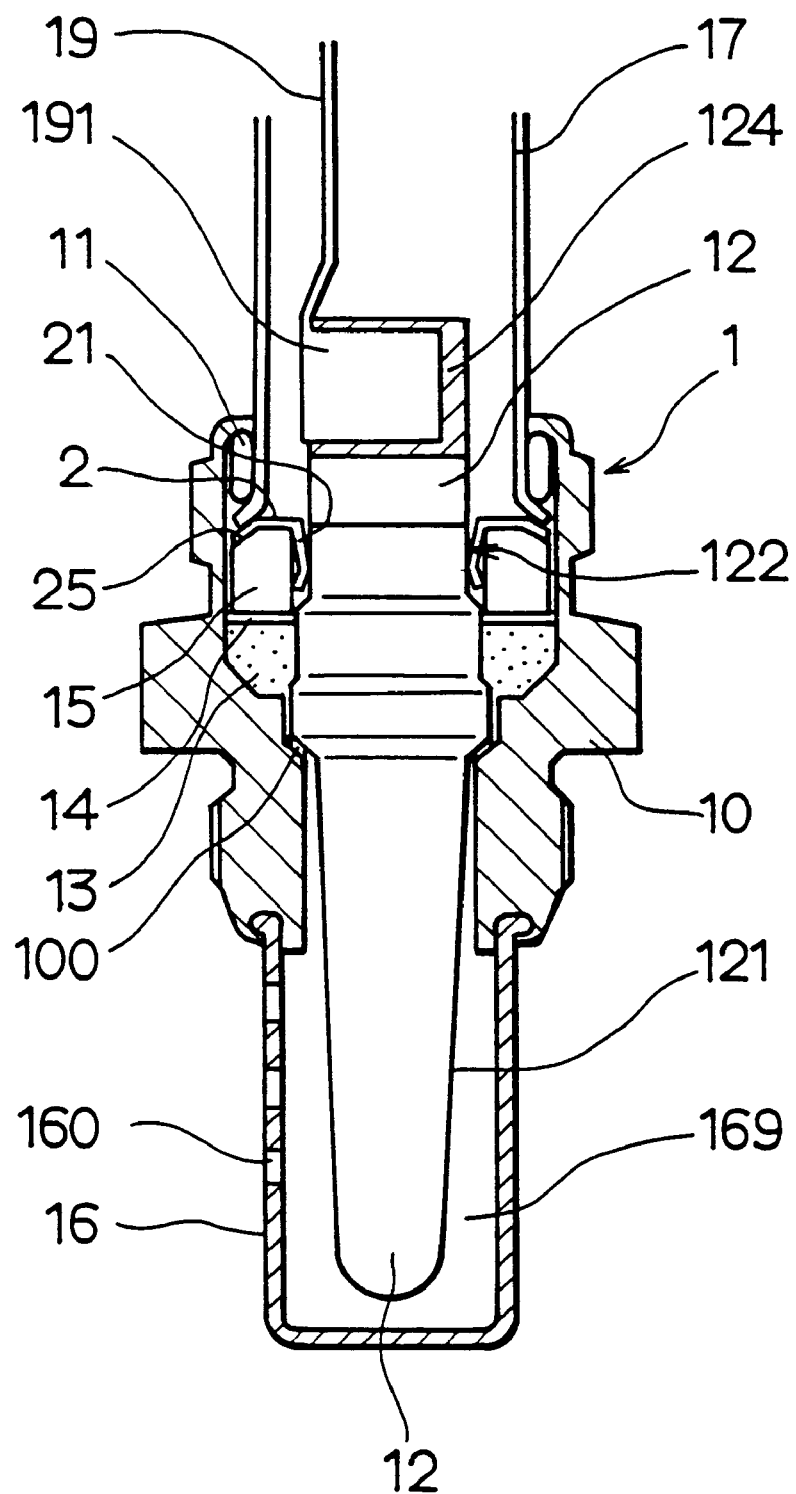
FIG. 1 is a partial cross-sectional view illustrating a main portion of an oxygen concentration detector according to a first embodiment of the present invention.

As illustrated in FIG. 1, the oxygen concentration detector 1 includes a cylindrical housing 10 and a detecting element 12 inserted into and disposed in the housing 10.

Powdery seal materials 13 made of ceramic powder are filled between an upper portion of the detecting element 12 and the housing 10. The detecting element 12 has, at an external portion thereof, an external electrode 121 and a lead portion 122 extending outwardly from the external electrode 121. A ring-shaped conducting member 2 for conducting electricity between the lead portion 122 of the detecting element 12 and the housing 10 is disposed between the lead portion 122 and the housing 10.

Figure 2:
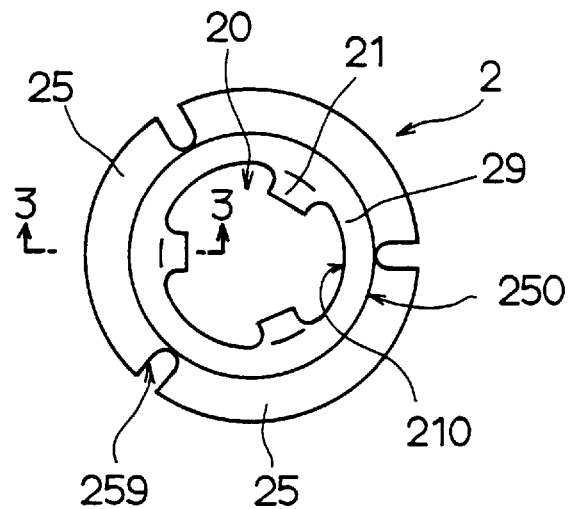
FIG. 2 is a front view illustrating a ring-shaped conducting member according to the first embodiment.
Figure 3:
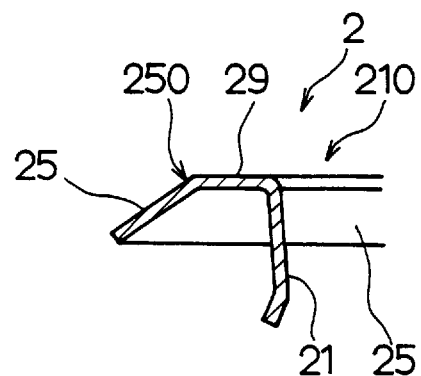
FIG. 3 is a cross-sectional view taken along line 3—3 in FIG. 2.

As illustrated in FIGS. 2 and 3, the ring-shaped conducting member 2 has a resilient contacting piece 21 in contact with the lead portion 122 at an inner periphery portion 210 of the conducting member 2. As illustrated in FIG. 2, a body 29 at the ring-shaped conducting member 2 is disposed at a top end side of an insulator 15.

The oxygen concentration detector 1 has a protecting cover 16 covering the outside of a lower portion of the detecting element 12. A measured gas chamber 169 is formed outside the detecting element 12 by the protecting cover 16.

Measured gas is introduced into the measured gas chamber 169 from measured gas introducing ports 160 disposed on the protecting cover 16. An upper portion of the protecting cover 16 is fixed at a bottom end of the housing 10.

Next, the oxygen concentration detector 1 has an air side cover 17 for covering the outside of the upper portion of the detecting element 12. The air side cover 17 is fixed to the housing 10 through the metallic ring 11 at the top end of the insulator 15. The air side cover 17 and the housing 10 may be considered to be external members of the detector 1.

The powdery seal materials 13 are filled under pressure between the detecting element 12 and the housing 10 while maintaining sealing performance by a pad 14 and the insulator 15 so that gas does not pass between an air chamber (not illustrated) inside the detecting element 12 and the measured gas chamber 169.

An internal electrode is installed on an interior surface of the air chamber provided inside the detecting element 12. A lead portion 124 is extended from the internal electrode to a top end of an outside portion of the detecting element 12. A lead wire (not shown) conducting electricity from an outside power source (not shown) is connected to the lead portion 124 from the connecting piece 191 through the terminal 19.

An outside surface of the detecting element 12 is covered with a platinum film. In the platinum film, a portion for carrying out an oxygen concentration detection by being in contact with the measured gas is the external electrode 121, while a portion positioned above a portion filled with the powdery seal materials 13 without being in contact with the measured gas is the lead portion 122.

When a heater (not shown) is provided in the air chamber of the detecting element 12, a heating portion at the heater is positioned at a tip end portion of the detecting element 12. A seating 100 is illustrated in FIG. 1.

As illustrated in FIGS. 2 and 3, the overall ring-shaped conducting member 2 is made of heat resisting alloy having a thin plate shape, and the ring-shaped conducting member 2 includes a ring-shaped body 29 and a receiving portion 20 for receiving the detecting element 12 surrounded by an inner peripheral portion 210 of the body 29. Three resilient contacting pieces 21 are provided at the inner peripheral portion 210.

An outer peripheral portion 250 of the ring-shaped conducting member 2 has a resilient piece 25 in contact with a bottom end portion of the air side cover 17. Three notch portions 259 are made in the resilient piece 25 to increase resiliency. However, the notch portions 259 are not always necessary.

Next, an operational effect of the present embodiment is explained.

Figure 4:
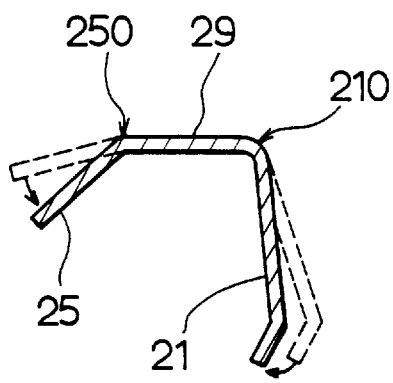
FIG. 4 is an explanatory view illustrating the ring-shaped conducting member according to the first embodiment.

As illustrated in FIG. 4, when the resilient contacting piece 21 and the resilient piece 25 of the ring-shaped conducting member 2 are assembled in the oxygen concentration detector 1, the resilient contacting piece 21 and the resilient piece 25 are bent from a state illustrated with a dotted line to a state illustrated with a solid line.

As illustrated in FIG. 1, at the resilient contacting piece 21, the resilient contacting piece 21 of the ring-shaped conducting member 2 and the lead portion 122 of the detecting element 12 are in contact with each other and the resilient piece 25 is in contact with the air side cover 17.

The lead portion 122 of the detecting element 12 conducts electricity to the housing 10 as a ground through the resilient contacting piece 21, the body 29, the resilient piece 25, the air side cover 17 and the metallic ring 11.

Therefore, since the oxygen concentration detector 1 of the present embodiment can conduct from the external electrode 121 without a lead wire being easily broken, an oxygen concentration detector having high reliability with respect to conductivity of the external electrode 121 can be obtained.

A conducting portion at the external electrode 121, that is, a position of the ring-shaped conducting member 2, is at the upper portion of the detecting element 12, which is at a low temperature. Thus, conducting malfunction due to heat oxidization of the external electrode 121 can be prevented.

The ring-shaped conducting member 2 is resiliently in contact with the detecting element 12, the housing 10 or the like. Therefore, even though the housing 10 or the like is deformed, the ring-shaped conducting member 2 is still in contact with the detecting element 12, the housing 10 or the like.

In a process of assembling the oxygen concentration detector 1, an assembling operation in which the lead wire and the terminal assembled at the external electrode 121 is removed, and therefore, ease of assembly is increased.

The lead portion 124 for conducting electricity to the internal electrode is installed on a head portion of the detecting element 12. The ring-shaped conducting member 2 is disposed to surround an outer periphery below the head portion of the detecting element 12. Therefore, a portion between the external electrode 121 and the internal electrode does not short.

Thus, according to the present embodiment, an oxygen concentration detector easily assembled without producing conducting malfunctions at the external electrode can be provided.

In the oxygen concentration detector 1 illustrated in FIG. 5, a protection layer 129 for protecting the device from corrosive materials in exhaust gas as measured gas is provided on a surface of the external electrode 121 and a surface below the lead portion 122 of the detecting element 12.

The ring-shaped conducting member 2 is disposed above the powdery seal materials 13. The protection layer 129 is provided on the part of the external electrode 121 exposed in the measuring chamber 169 and on the part of the lead portion 122 (below the powdery seal materials 13) also exposed in the measuring chamber 169.

Figure 5:
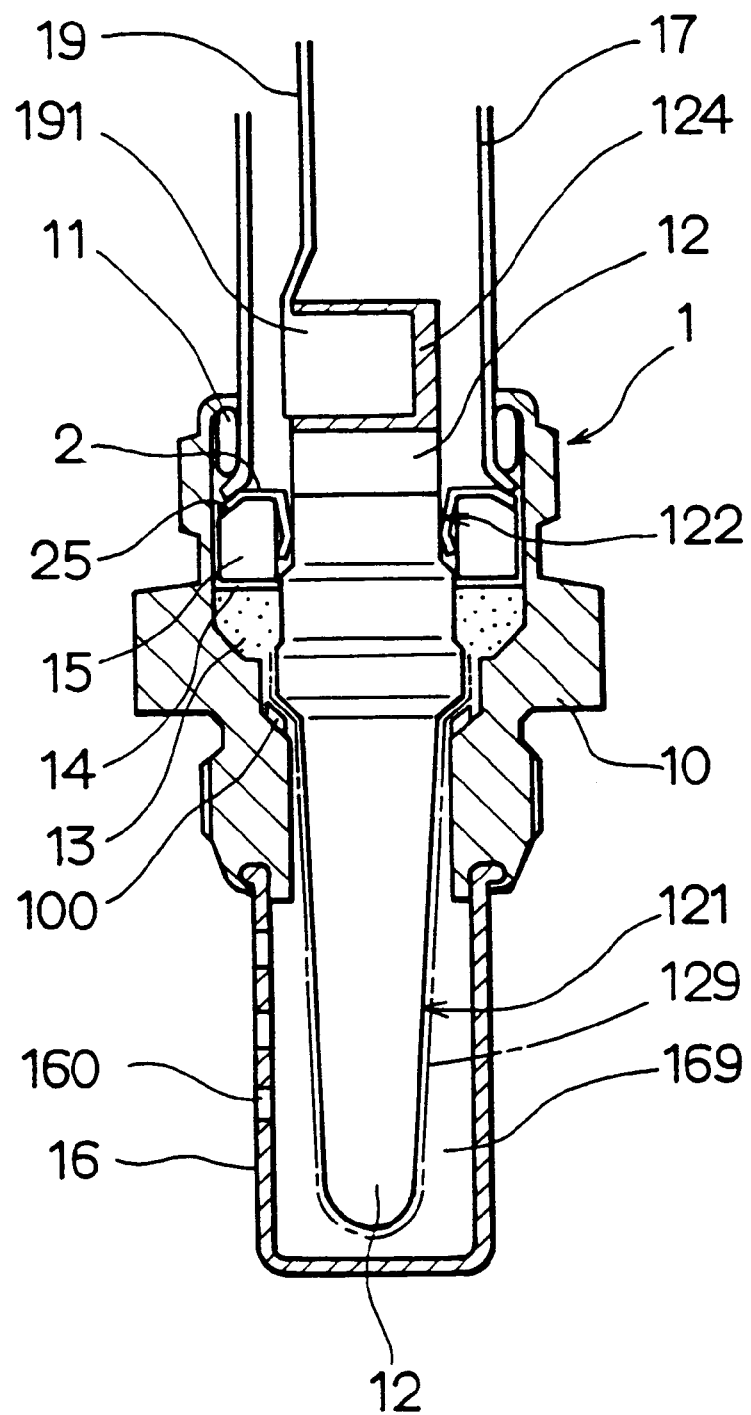
FIG. 5 is a partial cross-sectional view illustrating a main portion of another oxygen concentration detector according to the first embodiment.

According to the structure illustrated in FIG. 5, protection of the external electrode 121 by the protection layer 129 and the conductivity between the external electrode 121 and the housing 10 can be obtained.

(Second Embodiment)

Figure 6:
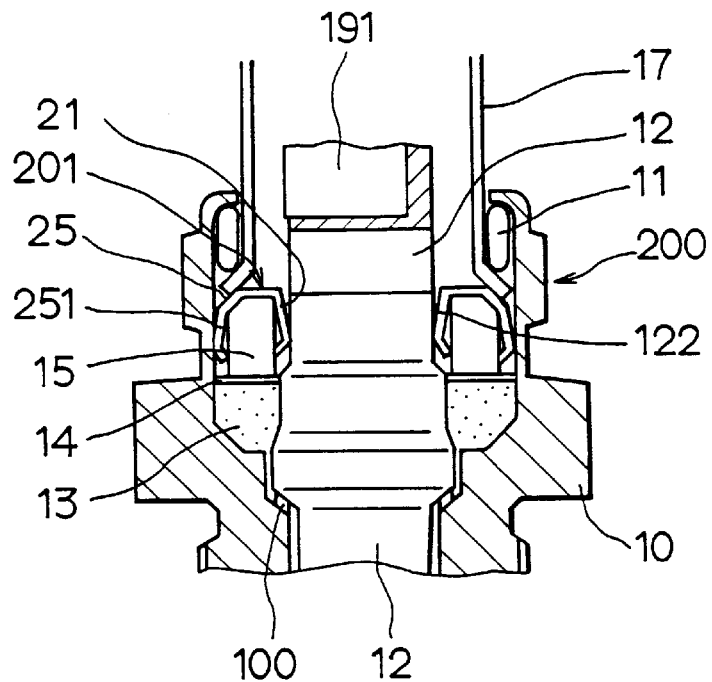
FIG. 6 is a partial cross-sectional view illustrating a main portion of an oxygen concentration detector according to a second embodiment of the present invention.
Figure 7:
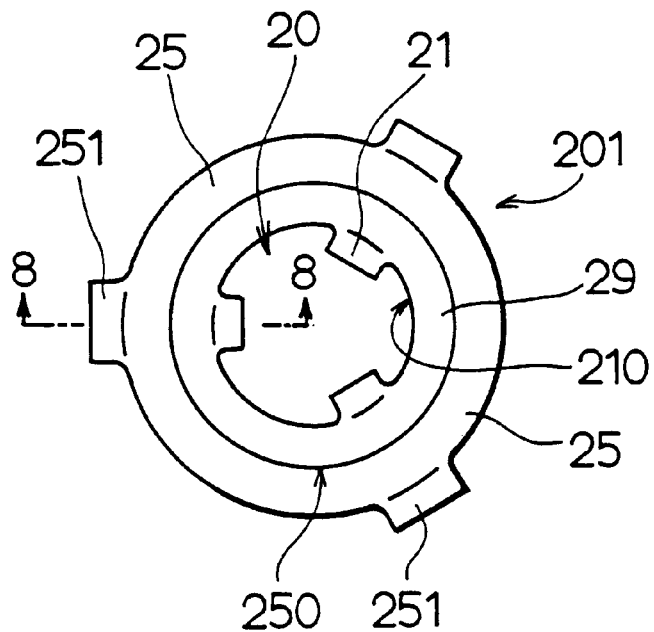
FIG. 7 is a front view illustrating a ring-shaped conducting member according to the second embodiment.
Figure 8:
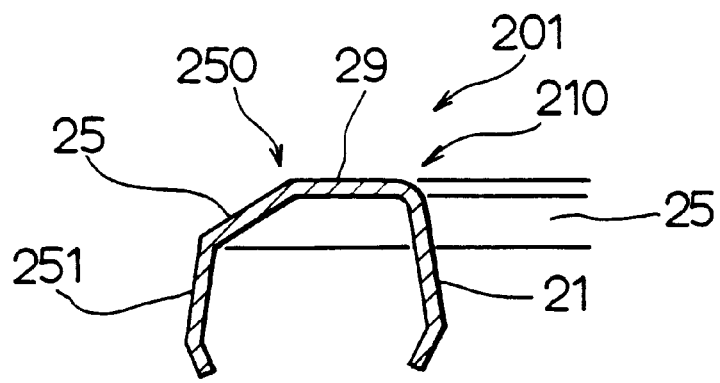
FIG. 8 is a cross-sectional view taken along line 8—8 in FIG. 7.

As illustrated in FIGS. 6 through 8, the oxygen concentration detector 200 in a second embodiment has three resilient contacting pieces 251 on ring-shaped conducting member 201.

As illustrated in FIG. 6, the oxygen concentration detector 200 has a structure in which the resilient contacting pieces 251 of the ring-shaped conducting member 201 are in contact with the housing 10.

As illustrated in FIGS. 7 and 8, the resilient contacting pieces 251 are provided to protrude outwardly from the resilient piece 25. The remaining structure of the oxygen concentration detector 200 in the second embodiment is the same as the first embodiment.

In the oxygen concentration detector 1 of the second embodiment, since the ring-shaped conducting member 201 is directly in contact with the housing 10 which functions as ground reliability of electric conductivity therebetween is increased even more.

An operational effect of the oxygen concentration detector 200 in the second embodiment is the same as the detector 1 in the first embodiment.

(Third Embodiment)

Figure 9:
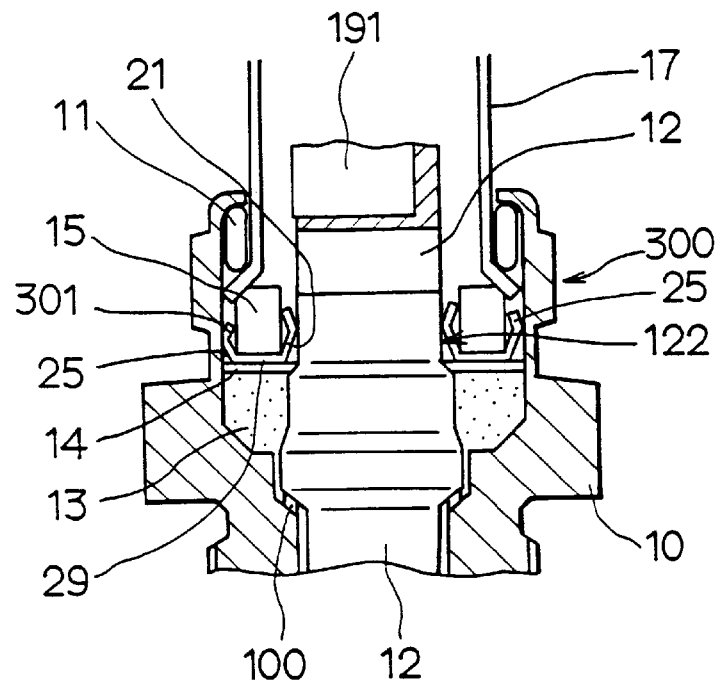
FIG. 9 is a partial cross-sectional view illustrating a main portion of an oxygen concentration detector according to a third embodiment of the present invention.

As illustrated in FIG. 9, the oxygen concentration detector 300 in a third embodiment has a structure in which the body 29 of the ring-shaped conducting member 301 is disposed between the pad 14 and the insulator 15.

The oxygen concentration detector 300 has the body 29 and the receiving portion for inserting the detecting element 12 installed at an inner peripheral portion of the body 29 and the ring-shaped conducting member 301 having the resilient piece 25 at an outer periphery of the body 29.

The ring-shaped conducting member 301 has a U-shaped cross-section on the pad 14, which is vertical relative to the first and the second embodiments. The other structure is the same as the first embodiment.

In the oxygen concentration detector 300 of the third embodiment, since the ring-shaped conducting member 301 is directly in contact with the housing 10, reliability of the conductivity therebetween is increased.

An operational effect of the third embodiment is the same as the first embodiment.

(Fourth Embodiment)

Although the first through third embodiments describe oxygen concentration detectors having the test-tube-shaped detecting element, in a fourth embodiment illustrated in FIGS. 10 through 13, the oxygen concentration detector 400 has a laminated layer-type detecting element 229. The laminated layer-type detecting element 229 has an overall shape of a flat board and has a heater integrally disposed inside the detecting element 229.

Figure 10:
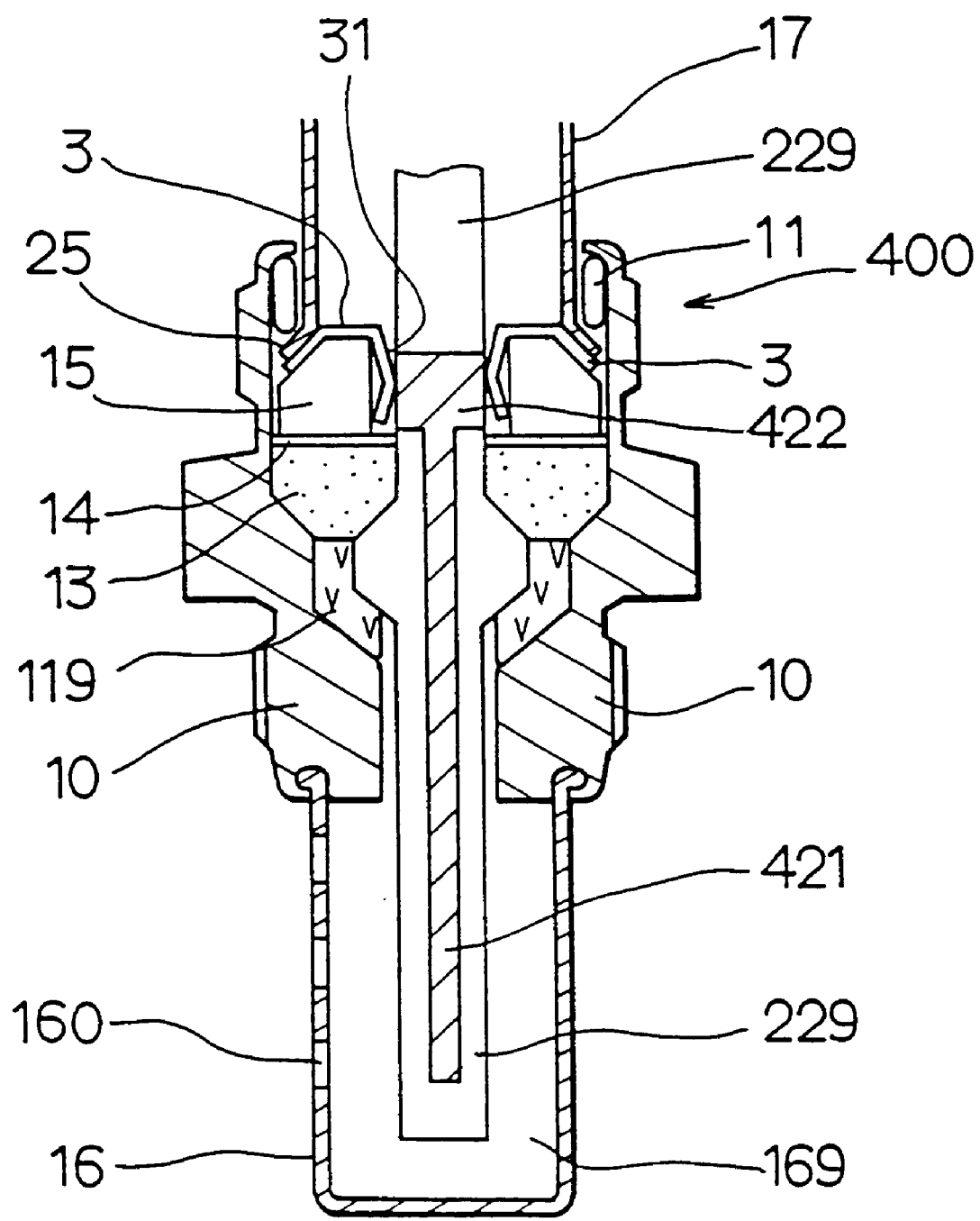
FIG. 10 is a partial cross-sectional view illustrating a main portion of an oxygen concentration detector according to a fourth embodiment of the present invention.

As illustrated in FIG. 10, the oxygen concentration detector 400 includes a cylindrical housing 10 and a laminated layer-type detecting element 229 inserted into and disposed in the housing 10.

The powdery seal materials 13 made of ceramic powder are filled under pressure between a top portion of the detecting element 229 and the housing 10. The detecting element 229 has an external electrode 421 and a lead portion 422 extending upwardly from the external electrode 421 at an outside surface of the detecting element 229. An insulator 119 is illustrated in FIG. 10.

Figure 11:
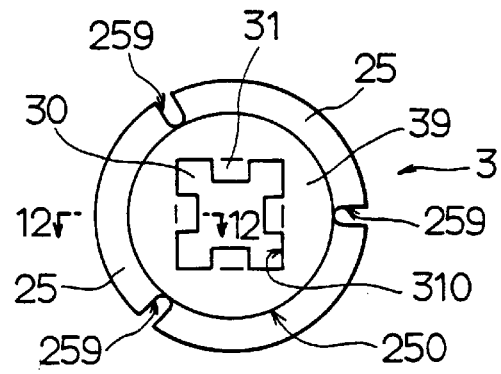
FIG. 11 is a front view illustrating a ring-shaped conducting member according to the fourth embodiment.
Figure 12:
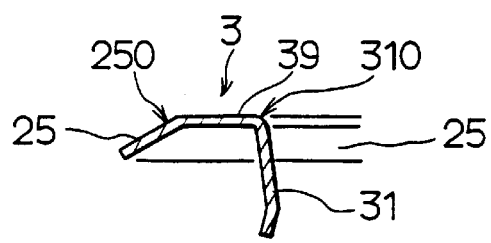
FIG. 12 is a cross-sectional view taken along line 12—12 in FIG. 11.

As shown in FIG. 10, a ring-shaped conducting member 3 for conducting electricity is disposed between the lead portion 422 of the laminated layer-type detecting element 229 and the housing 10 to conduct electricity therebetween and has four resilient contacting pieces 31 in contact with the lead portion 422 at an inner peripheral portion 310 (see FIGS. 11 and 12).

As illustrated in FIGS. 11 and 12, the overall ring-shaped conducting member 3 is made of a heat resisting alloy having a thin plate shape and the ring-shaped conducting member 3 includes a ring-shaped body 39 and a receiving portion 30 which is for receiving the detecting element 229 and is surrounded by the inner peripheral portion 310 of the body 39.

The receiving portion 30 has the same shape as the transverse cross-section of the detecting element 229. The resilient contacting piece 310 is provided at each of four sides of the inner peripheral portion 310.

The other structure is the same as the first embodiment.

Figure 13:
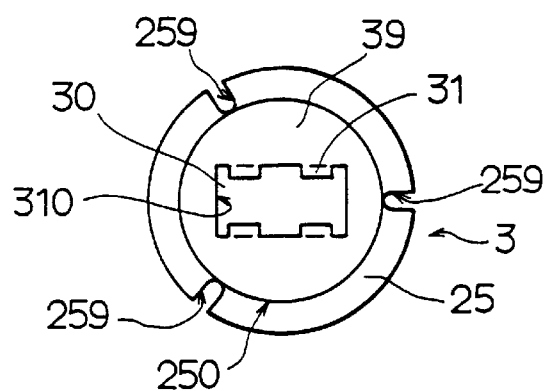
FIG. 13 is a front view illustrating another ring-shaped conducting member according to the fourth embodiment.
Figure 14:
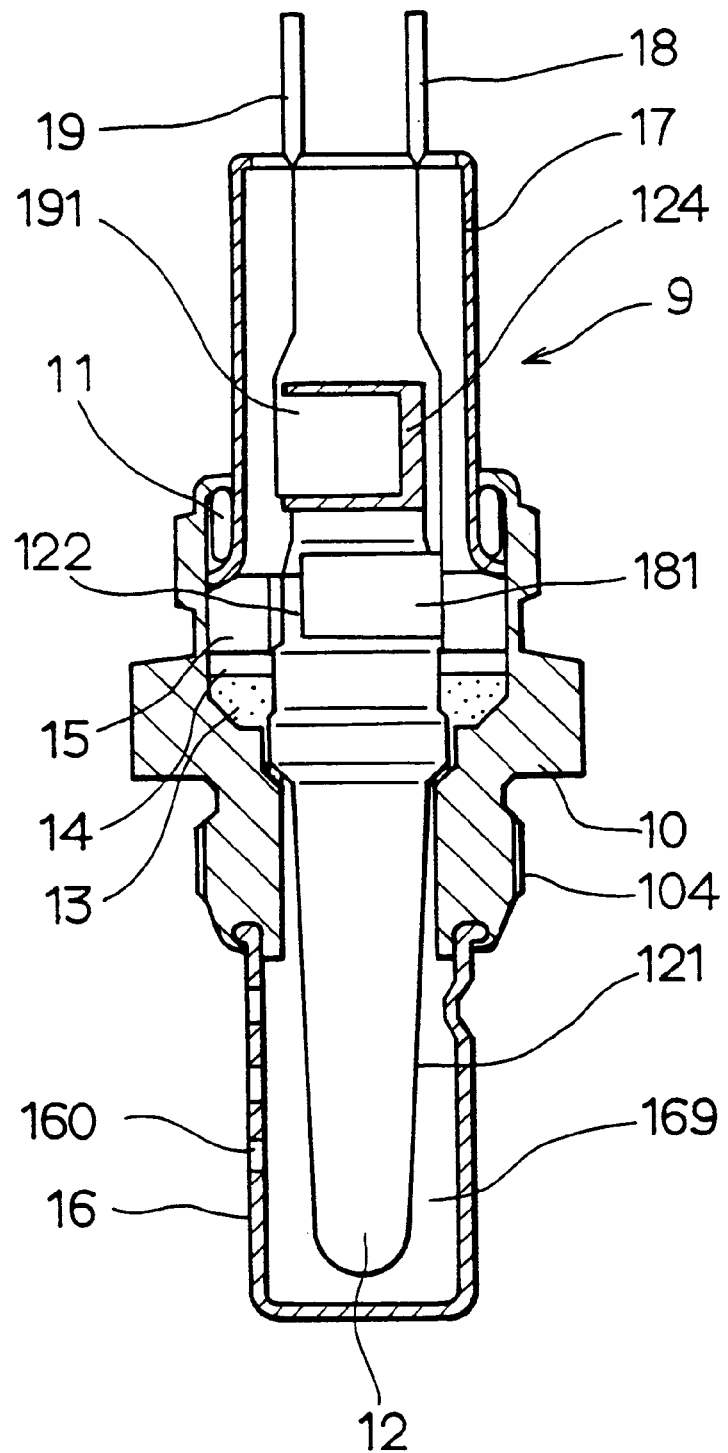
FIG. 14 is a partial cross-sectional view illustrating a main portion of a conventional oxygen concentration detector.

As illustrated in FIG. 13, when the cross-sectional shape of the detecting element 229 may be a rectangle, and in that case, a pair of resilient contacting pieces 310 are provided at each of two places on each of the long sides of the rectangle which face with each other.

The other structure is the same as the first embodiment, and the oxygen concentration detector 400 of the fourth embodiment has the same operational effect as the first embodiment.

The present invention having been described should not be limited to the disclosed embodiments, but it may be modified in many other ways without departing from the scope and the spirit of the invention. For example, the laminated layer-type detecting element 229 can be used in the second and the third embodiments. Such changes and modifications are to be understood as being included with the scope of the present invention as defined by the appended claims.

What is claimed is:

1. An oxygen concentration detector, comprising:

a cylindrical housing;

a detecting element, disposed inside said housing, for being exposed to measurement gas; and powdery seal materials made of ceramic powder, said powdery seal materials filled with pressure between a tip portion of said detecting element and said housing;

wherein said detecting element includes an internal electrode on an inside surface thereof, and an external electrode on an outside surface thereof for being exposed to said measurement gas, and a lead portion extending from said external electrode, said oxygen concentration detector further including:

a one-piece ring-shaped conductive member provided between said lead portion of said external electrode and said housing, for conducting electricity therebetween, said ring-shaped conductive member having a resilient contacting piece biased toward a center of said ring-shaped conductive member to contact said lead portion at an inner peripheral portion of said ring-shaped conductive member;

wherein said powdery seal material forms a gas-tight seal separating said external electrode from said conductive member.

2. An oxygen concentration sensor according to claim 1, wherein said ring-shaped conductive member has a plurality of resilient contacting pieces, biased toward said center of said ring-shaped conductive member to contact said lead portion of said external electrode, at said inner peripheral portion of said ring-shaped conductive member.

3. An oxygen concentration detector according to claim 2, wherein an outer peripheral portion of said ring-shaped conductive member has a resilient piece, biased away from said center of said ring-shaped conductive member to contact said housing.

4. An oxygen concentration detector according to claim 3, wherein said outer peripheral portion has a plurality of resilient contacting pieces biased away from said center of said ring-shaped conductive member to contact said housing.

5. An oxygen concentration detector according to claim 1, wherein said ring-shaped conductive member has a resilient piece, biased away from said center of said ring-shaped conductive member to contact said housing at an outer peripheral portion of said ring-shaped conductive member.

6. An oxygen concentration detector according to claim 5, wherein said outer peripheral portion has a plurality of resilient contacting pieces biased away from said center of said ring-shaped conductive member to contact said housing.

7. An oxygen concentration detector according to claim 5, wherein said resilient piece directly contacts said housing.

8. An oxygen concentration detector according to claim 5, further comprising an insulator located around an upper periphery of said detecting element;

wherein a portion of said ring-shaped conductive member adjacent said resilient piece biased away from said center of said ring-shaped conductive member is fixed between said housing and said insulator to enable said resilient piece biased toward the center of said ring-shaped conductive member to be so biased.

9. A gas concentration detector comprising:

an external member;

a gas detecting element having a first end disposed proximate to an end of said external member and a second end extending from said external member to terminate at an external electrode, a surface of said first end being electrically conductive;

a one-piece conductive member disposed between said gas detecting element and said external member, said conductive member having a resilient contacting piece biased in a radial direction toward at least one of said gas detecting element and said external member to establish electrical contact therebetween; and sealing means for forming a gas-tight seal separating said conductive member from said external electrode.

10. A gas concentration detector according to claim 9, wherein said external member is an air side cover.

11. A gas concentration detector according to claim 9, wherein said external member is a housing.

12. A gas concentration detector according to claim 9, wherein said conductive member comprises:

a resilient contacting piece biased toward a center of said conductive member to contact said detecting element; and a resilient piece biased away from said center of said conductive member to contact said external member.

13. A gas concentration detector according to claim 9, wherein a surface of a portion of said detecting element proximate to said second end is not electrically conductive.

14. A gas concentration detector according to claim 9, further comprising:

an additional external member disposed proximate to said end of said external member and around a portion of said detecting element, said external member, said additional external member and said portion of said detecting element collectively defining a volume therebetween; and an insulator disposed in a portion of said volume proximate said first end of said detecting element;

wherein said conductive member covers an end of said insulator; and said sealing means includes sealing material disposed in a portion of said volume proximate said second end of said detecting element to form said gas-tight seal between said detecting element and one of said external member and said additional external member.

15. A gas concentration detector according to claim 14, wherein said additional external member is an air side cover.

16. A gas concentration detector according to claim 14, wherein said additional external member is a housing.

17. A gas concentration detector according to claim 14, wherein said conductive member covers an end of said insulator proximate said first end of said detecting element.

18. A gas concentration detector according to claim 14, wherein said conductive member covers an end of said insulator most proximate said second end of said detecting element.

19. A gas concentration detector according to claim 14, wherein said resilient contacting piece is biased toward said additional external member to physically and electrically contact said additional external member.

20. A gas concentration detector according to claim 9, further comprising;

an additional external member disposed proximate to said end of said external member and around a portion of said detecting element;

wherein said resilient contacting piece is biased toward said additional external member to physically and electrically contact said additional external member.

21. An oxygen concentration detector comprising:

a cylindrical housing;

a detecting element, a portion of which is disposed inside said housing, for being exposed to measurement gas;

a cover, a portion of said detecting element outside of said housing being disposed inside said cover; and powdery seal materials made of ceramic powder, said powdery seal materials filled with pressure between a tip portion of said detecting element and said housing, wherein said detecting element includes an internal electrode on an inside surface thereof, and an external electrode on an outside surface thereof for being exposed to said measurement gas, and a lead portion extending from said external electrode, said oxygen concentration detector further including:

a one-piece ring-shaped conductive member provided between said lead portion of said external electrode and said cover, for conducting electricity therebetween, said ring-shaped conductive member having a resilient contacting piece extending therefrom and biased toward a center of said ring-shaped conductive member to contact said lead portion at an inner peripheral portion of said ring-shaped conductive member;

wherein said powdery seal material forms a gas-tight seal separating said external electrode from said conductive member.

22. An oxygen concentration sensor according to claim 21, wherein said ring-shaped conductive member has a plurality of resilient contacting pieces, biased toward said center of said ring-shaped conductive member to contact said lead portion of said external electrode, at said inner peripheral portion of said ring-shaped conductive member.

23. An oxygen concentration detector according to claim 22, wherein an outer peripheral portion of said ring-shaped conductive member has a resilient piece, biased away from said center of said ring-shaped conductive member to contact said cover.

24. An oxygen concentration detector according to claim 23, wherein said outer peripheral portion has a plurality of resilient contacting pieces biased away from said center of said ring-shaped conductive member to contact said cover.

25. An oxygen concentration detector according to claim 21, wherein said ring-shaped conductive member has a resilient piece, biased away from said center of said ring-shaped conductive member to contact said cover at an outer peripheral portion of said ring-shaped conductive member.

26. An oxygen concentration detector according to claim 25, wherein said outer peripheral portion has a plurality of resilient contacting pieces biased away from said center of said ring-shaped conductive member to contact said cover.

27. An oxygen concentration detector according to claim 21, wherein said resilient contacting piece is located on an outer peripheral portion of said ring-shaped conductive member, thereby to apply pressure in a direction in which it contacts said cover.

* * * * *